US00PP09033P

United States Patent [19]

Meilland

[11] Patent Number: Plant 9,033

[45] Date of Patent: Jan. 3, 1995

[54] MINIATURE ROSE PLANT NAMED MEIFRUIJE

[75] Inventor: Alain A. Meilland, Antibes, France

[73] Assignee: The Conard-Pyle Company, West Grove, Pa.

[21] Appl. No.: 227,276

[22] Filed: Apr. 13, 1994

[51] Int. Cl.[6] ..... A01H 5/00
[52] U.S. Cl. ..... Plt./7.1
[58] Field of Search ..... Plt. 7.1, 8.2

*Primary Examiner*—Howard J. Locker
*Attorney, Agent, or Firm*—Burns, Doane, Swecker & Mathis

[57] ABSTRACT

A new and distinct variety of rose plant of the Miniature Class is provided which forms attractive bicolored blossoms which are yellow edged with a suffusion of Persimmon Orange in coloration. The plant is bushy, and forms very strong vegetation that is dense and glossy in appearance. The foliage coloration and glossy appearance attractively contrast with the distinctive relatively light bicolored blossom coloration. The blossoms possess no fragrance. The plant is particularly well-suited for growing as attractive diminutive ornamentation in the landscape.

1 Drawing Sheet

SUMMARY OF THE INVENTION

The new variety of Miniature rose plant was created by articicial pollination wherein two parents were crossed which previously had been studied in the hope that they would contribute the desired characteristics. The female parent (i.e., the seed parent) was the product of the crossing of the Savamark variety (non-patented in the United States) by the Meitrisical variety (non-patented in the United States). The male parent (i.e., the pollen parent) of the new variety was the Meigronuri variety (U.S. Plant Pat. No. 4,625). The parentage of the new variety can be summarized as follows:

(SAVAMARK×MEITRISICAL)×MEIGRONURI.

The seeds resulting from the above pollination were sown and small plants were obtained which were physically and biologically different from each other. Selective study resulted in the identification of a single plant of the new variety.

It was found that the new variety fo Miniature rose plant of the present invention possesses the following combination of characteristics:

(a) forms attractive bicolored blossoms which are yellow edged with a suffusion of Persimmon Orange in coloration,
(b) forms dense and glossy foliage,
(c) exhibits a bushy growth habit, and
(d) is particularly well-suited for growing as attractive diminutive ornamentation in the landscape.

The distinctive bicolored blossom coloration is believed to be new in the miniature rose Class. The foliage coloration and glossy appearance attractively contrast with the relatively light bicolored blossom coloration.

The new variety well meets the needs of the horticultural industry. It is particularly well-suited for growing outdoors in order to enhance the appearance of the surroundings.

The new variety has been found to undergo asexual propogation in France by a number of routes, including budding, grafting, and cuttage. Asexual propagation by the above-mentioned methods as performed in France has shown that the characteristics of the new variety are strictly transmissible from one generation to another.

The new variety has been named the Meifruije variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were two years of age and were observed during September while growing on their own roots in greenhouses at Le Cannet des Maures, Var, France.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets with the upper surface being shown at the top left and the under surface being shown at the bottom right;

FIG. 15—illustrates specimens of leaves with five leaflets with the upper surface being shown at the bottom and the under surface being shown at the top; and FIG. 16—illustrates specimens of leaves with seven leaflets with the upper surface being shown at the top and the under surface being shown at the bottom.

DETAILED DESCRIPTION

Figures 1, 2, 3, 4, 5, 6, 7, 8, 9, 10, 11, 12, 13, 14, 15, 16:
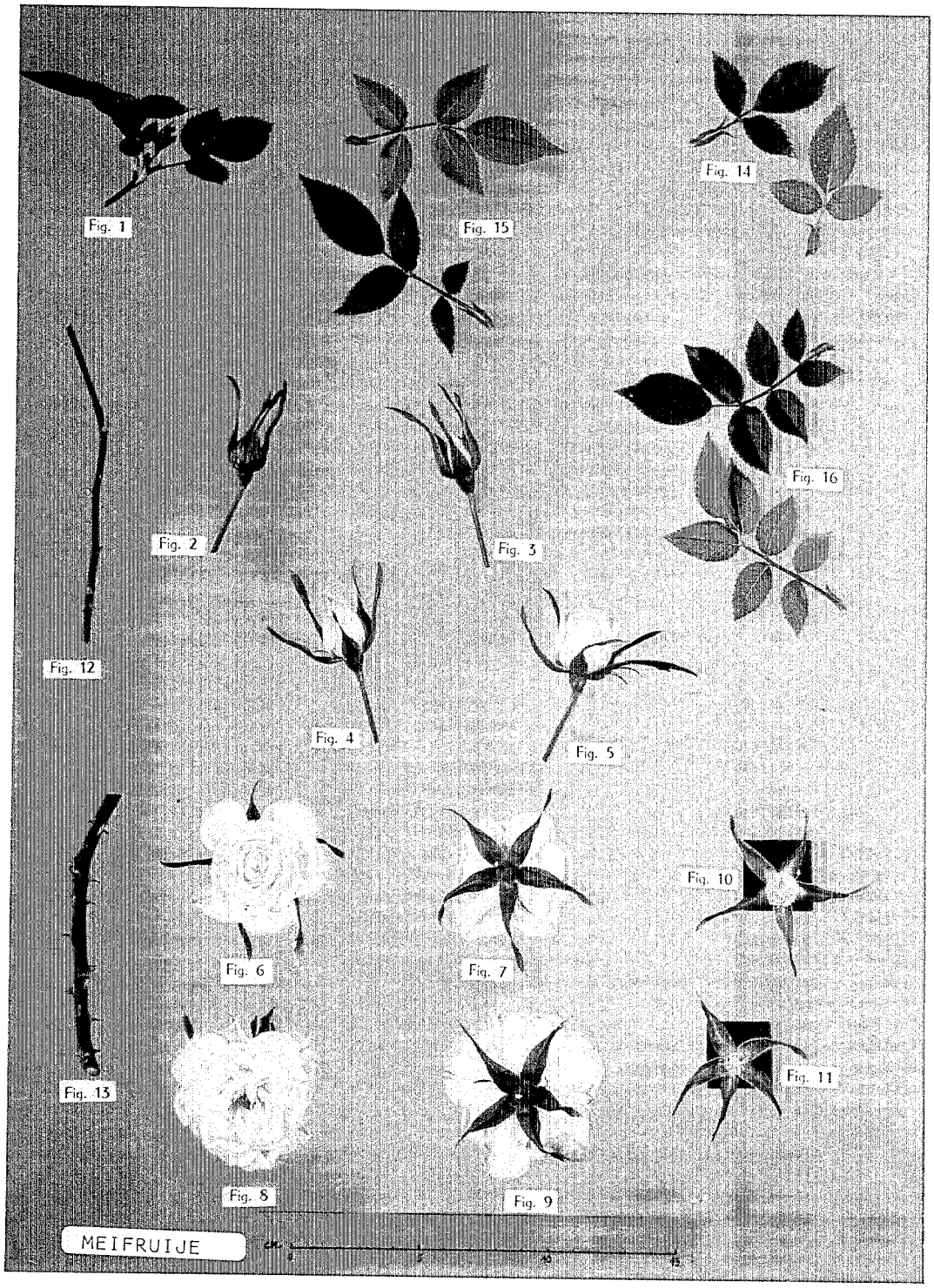

The chart used in the identification of the colors is that of The Royal Horticultural Society (R.H.S. Colour Chart). The terminology which precedes reference to the chart has been added to indicate the corresponding colors in more common terms. The description is based on two year-old specimens of the new variety which were observed during Septemper while growing on their own roots in greenhouses at Le Cannet des Maures, Var, France.

Class: Miniature.

Plant:

*Height.*—Approximately 30 to 35 cm. on average at the end of the growing season.

*Habit.*—Bushy.

Branches:

*Color.*—Young stems: green, Green Group 143B, and widely suffused with reddish coloration. Adult wood: medium green, Green Group 137A.

*Thorns.*—Size: small. Quantity: few. Color: reddish on young stems and pinkish on adult wood.

Leaves:

*Petioles.*—Upper surface: striped, reddish on young foliage and medium green on mature foliage with more or less glandular edges. Under surface: light green with some thorns.

*Stipules.*—Adnate, pectinate, wide and linear.

*Leaflets.*—Number: 3, 5 (most often), and 7. Shape: elliptic. Serration: simple and regular. Texture: consistent. General appearance: dense, medium green, and glossy. Color (young foliage): Upper surface: medium green, Green Group 143A, and more or less edged and suffused with reddish brown coloration. Under surface: medium green, Green Group 143B, and more or less suffused with reddish-brown coloration. Color (adult foliage): Upper surface: dark green, Green Group 137A. Under surface: light green, Green Group 137C.

Inflorescence:

*Number of flowers.*—Approximately 1 to 5 per stem.

*Peduncle.*—Light green, and its length is approximately 3 cm. on average.

*Sepals.*—Upper surface: tomentose and greenish in coloration. Under surface: medium green with appendiculated edges.

*Buds.*—Shape: ovoid. Length: approximately 1.5 to 2 cm. on average. Size: small. Color upon opening: Upper surface: intense Persimmon Orange, Orange Group 28A, and Buttercup Yellow, Yellow-Orange Group 15B at the base. Under surface: Lemon Yellow, Yellow Group 13C, and slightly suffused with Capsicum Red, Orange-Red Group 33A.

*Flower.*—Form: flat. Diameter: approximately 5 cm. on average. Color (when opening begins): Upper surface: light Buttercup Yellow, Yellow-Orange Group 15C, and edged with a suffusion of Persimmon Orange, Orange Group 28A. Under surface: Aureolin, Yellow Group 12B, and more or less edged with a suffusion of Capsicum Red, Orange-Red Group 33A. Color (when blooming): Upper surface: light Buttercup Yellow, Yellow-Orange Group 15C, and edged with a suffusion of Persimmon Orange, Orange Group 28A. Under surface: Aureolin, Yellow Group 12B, and more or less edged with a suffusion of Capsicum Red, Orange-Red Group 33A. Color (at end of blooming): Upper surface: light Lemon Yellow, Yellow Group 13C, and edged with scarlet pink and more or less suffused with Fire Red, Orange-Red Group 33B at the center. Under surface: light Lemon Yellow, Yellow-Orange Group 13C, and edged with scarlet pink and more or less suffused with Fire Red, Orange-Red Group 33B at the center. Fragrance: none. Lasting quality: long. Petal shape: oval with cordate base. Petal drop: good. Anthers: normal and golden yellow in coloration. Stamen number: approximately 51 on average. Filaments: short and bright yellow in coloration. Pistils: strawlike in coloration. Stigmas: normal. Styles: greenish in coloration. Receptacle: medium green, smooth, and in longitudinal section in the shape of a funnel.

Development:

*Vegetation.*—Very strong.

*Blooming.*—Normal.

*Aptitude to bear fruit.*—Normal.

*Resistance to diseases.*—Good.

I claim:

1. A new and distinct variety of miniature rose plant characterized by the following combination of characteristics:

(a) forms attractive bicolored blossoms which are yellow edged with a suffusion of Persimmon Orange in coloration, (b) forms dense and glossy foliage, (c) exhibits a bushy growth habit, and (d) is particularly well-suited for growing as attractive diminutive ornamentation in the landscape;

substantially as herein shown and described.

* * * * *

MEIFRUIJE
cm.
0
5
10
15